United States Patent [19]

Roman et al.

[11] 4,292,325
[45] Sep. 29, 1981

[54] OXYIMINO-SUBSTITUTED (1R,CIS)CYCLOPROPANECARBOXYLATE PESTICIDES

[75] Inventors: Steven A. Roman, Oakdale; Samuel B. Soloway, Modesto, both of Calif.

[73] Assignee: Shell Oil Company, Houston, Tex.

[21] Appl. No.: 178,336

[22] Filed: Aug. 15, 1980

Related U.S. Application Data

[63] Continuation-in-part of Ser. No. 13,841, Feb. 21, 1979, which is a continuation-in-part of Ser. No. 911,743, Jun. 2, 1978, abandoned.

[51] Int. Cl.³ .................... A01N 53/00; C07C 131/02
[52] U.S. Cl. ................... 424/304; 260/465 D; 260/544 L; 424/305; 562/506
[58] Field of Search .............. 260/465 D, 544 L; 560/124; 424/304, 305; 562/506

[56] References Cited
U.S. PATENT DOCUMENTS
3,922,269  11/1975  Elliott et al.

OTHER PUBLICATIONS
Elliott, M. et al., J. Chem. Soc. Perkin I, pp. 2470–2474 (1974).

Primary Examiner—Dolph H. Torrence

[57] ABSTRACT (1R,cis)-cyclopropane compounds, substantially free of other stereoisomers, and having the formula

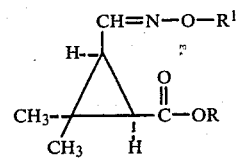

wherein $R^1$ is $C_{3-6}$ alkyl and R is α-cyano-3-phenoxybenzyl or 3-phenoxybenzyl, are highly active pesticides.

14 Claims, No Drawings

OXYIMINO-SUBSTITUTED (1R,CIS)CYCLOPROPANECARBOXYLATE PESTICIDES

CROSS-REFERENCE TO RELATED APPLICATIONS

This application is a continuation-in-part of Ser. No. 13,841, filed Feb. 21, 1979, which is a continuation-in-part of Ser. No. 911,743, filed June 2, 1978, now abandoned.

BACKGROUND OF THE INVENTION

1. Field of the Invention

This invention is directed to new oxyimino-substituted compounds, their use as pesticides, to pesticidal formulations containing these new compounds and to certain novel intermediates.

2. Description of the Prior Art

U.S. Pat. No. 3,922,269 describes a class of 2,2-dimethyl-3-(oxyiminomethyl)cyclopropanecarboxylic acid esters useful as insecticides. In the case of such esters of α-substituted asymmetric alcohols, three asymmetric centers and one oxime double bond are present and therefore a total of sixteen theoretical stereoisomers are possible. Eight theoretical stereoisomers are possible when there is no asymmetric center in the alcohol moiety. The above-mentioned patent states that esters, in which the two hydrogen atoms on the cyclopropane ring are in the absolute stereochemical relationship equivalent to that in (+)-trans-chrysanthemic acid, tend to be among the most insecticidally active of the various isomers and are preferred for that reason. Indeed, only (1R,trans)-cyclopropanecarboxylate oximes were apparently prepared and tested, and form the basis of the working examples.

SUMMARY OF THE INVENTION

It has now been found that certain oxyimino-substituted cyclopropanecarboxylates derived from the (1R,cis)-form of 2,2-dimethyl-3-formyl-cyclopropanecarboxylic acid are useful pesticides (insecticides and acaricides) and exhibit high knockdown characteristics.

Therefore, this invention is directed to new (1R,cis)-cyclopropane compounds, substantially free of other stereoisomers, and having the formula

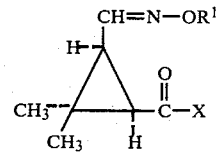

wherein $R^1$ is an alkyl group containing from 3 to 6 carbon atoms and X is chlorine, bromine or OR in which R is a hydrogen atom, a salt-forming cation, an alkyl group containing from 1 to 20 carbon atoms, α-cyano-3-phenoxybenzyl or 3-phenoxybenzyl, with the proviso that when R is α-cyano-3-phenoxybenzyl then the alcohol moiety is in the R,S-racemic or S-optical configuration.

The oxime substituent group of the compounds of the invention gives rise to geometric isomerism by virtue of the presence of an asymmetrically substituted double bond. These isomers are usually described as follows:

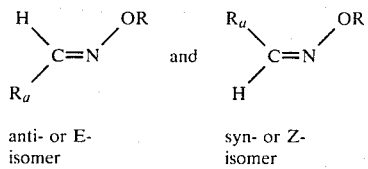

anti- or E-isomer    syn- or Z-isomer

A useful subclass of the invention comprises (1R,cis) esters in which the oxime substituent is in the Z-isomer form as such isomers can be several times more pesticidally active than when the oxime substituent is in the E-isomer form or is a mixture of the E- and Z-isomer forms.

Since the biological activity of various optical or geometric isomers and diastereoisomer pairs within the (1R,cis) esters of the invention may differ somewhat, it may be desirable to use a more active optical and/or geometric isomer or diastereoisomer pair of the invention substantially free of the other isomers or pair.

The (1R,cis) esters of the present invention wherein R represents α-cyano-3-phenoxybenzyl or 3-phenoxybenzyl are pesticidally active.

The other oxyimino-substituted (1R,cis)-cyclopropane compounds described above in which X is chlorine, bromine or OR in which R represents a hydrogen atom, a salt-forming cation or an alkyl group are useful intermediates for the production of the pesticidal esters.

When R is a salt-forming cation, it is selected from alkali metals, alkaline earth metals, aluminum, heavy metals, such as copper, silver, nickel and the like, ammonia or a tetrahydrocarbylammonium compound in which the total number of carbon atoms in the hydrocarbyl groups is between 4 and 70 carbon atoms. The hydrocarbyl groups can be alkyl, aryl, aralkyl and the like. Preferably, the hydrocarbyl groups are selected from alkyl groups containing from 1 to 10 carbon atoms and aralkyl groups containing from 7 to 10 carbon atoms.

When R is an alkyl group, it contains from 1 to 20 carbon atoms, and preferably from 1 to 6 carbon atoms, for example, methyl, ethyl, n-propyl, tert-butyl and the like.

In the pesticidal (1R,cis) esters of the invention, $R^1$ represents an alkyl group containing 3 to 6 carbon atoms, such as n-propyl, isopropyl, n-butyl, sec-butyl, isobutyl, tert-butyl, amyl, isoamyl, tert-amyl, n-hexyl and the like. Particularly suitable are those compounds wherein $R^1$ is an alkyl group containing 4 or 5 carbon atoms, particularly n-butyl, isobutyl, tert-butyl, 2-methylbutyl, n-pentyl or neopentyl.

Because of their pesticidal activity and ease of preparation, one preferred subclass of the invention are those esters wherein R is derived from 3-phenoxybenzyl alcohol. Examples of some highly active compounds of this subclass of the invention are:
3-phenoxybenzyl (1R,cis)-2,2-dimethyl-3-((neopentoxyimino)methyl)cyclopropanecarboxylate and
3-phenoxybenzyl (1R,cis)-2,2-dimethyl-3-((isobutoxyimino)methyl)cyclopropanecarboxylate.

Because of their pesticidal activity, another preferred subclass of the invention are those (1R,cis) esters derived from α-cyano-3-phenoxybenzyl alcohol, particularly in the S-optical configuration. In fact, the (1R,cis) esters wherein the alcohol substituent is in the R-α-cyano-3-phenoxybenzyl alcohol form are without practical insecticidal utility. Thus, one preferred embodiment of the invention is directed to those (1R,cis) esters derived from α-cyano-3-phenoxybenzyl alcohol in which such alcohol is in a racemic or, alternatively, in an S-optical configuration. Examples of some highly active compounds of this subclass of the invention are the following compounds wherein R is derived from α-cyano-3-phenoxybenzyl alcohol and $R^1$ is an alkyl containing 4 to 5 carbon atoms:

α-cyano-3-phenoxybenzyl (1R,cis)-2,2-dimethyl-3-((n-butoxyimino)methyl)cyclopropanecarboxylate, α-cyano-3-phenoxybenzyl (1R,cis)-2,2-dimethyl-3-((isobutoxyimino)methyl)cyclopropanecarboxylate, α-cyano-3-phenoxybenzyl (1R,cis)-2,2-dimethyl-3-((tert-butoxyimino)methyl)cyclopropanecarboxylate, and α-cyano-3-phenoxybenzyl (1R,cis)-2,2-dimethyl-3-((neo-pentoxyimino)methyl)cyclopropanecarboxylate which compounds are pesticidally active when the alcohol moiety is present in the R,S-racemic or S-optically active form, and particularly when the oxime substituent is in the Z-isomer form or in a mixture of the E- and Z-isomer forms.

A particularly preferred subclass of the invention are those (1R,cis) esters derived from the S-α-cyano-3-phenoxybenzyl alcohol and wherein the oxime substituent is the Z-isomer form.

It has been observed that esters, wherein the oxime substituent is in the Z-isomer form, are the most pesticidally active. Therefore, the Z-isomers (or mixtures of isomers in which the Z-isomer predominates) form another preferred subclass of the (1R,cis) esters of the invention. That the Z-isomer form is more pesticidally active contrasts with another class of oxime pesticides disclosed in U.S. Pat. No. 4,079,149, in which the E-isomer form is said to be the more pesticidally active of the oxime geometric isomer forms.

The pesticidal (1R,cis) esters of the present invention may be prepared by esterification involving the reaction of an alcohol or derivative thereof of formula RQ, e.g. of formula II, and a (1R,cis)-cyclopropane carboxylic acid or derivative thereof of formula III,

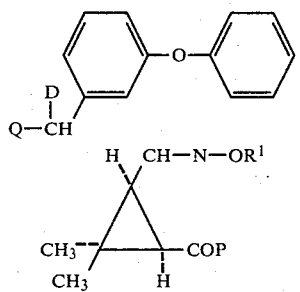

where Q and COP are functional groups or atoms which will react to form an ester linkage and D is CN or a hydrogen atom.

It is usually convenient in practice either to treat the acid or acid halide with the alcohol (COP=COOH or CO-halide and Q=OH) or to treat a halogeno compound (Q=halogen) with a salt of the carboxylic acid (COP=COO—M where M is, for example, a silver or triethylammonium cation).

Transesterification is not always practical and, it is useful to prepare the intermediate (1R,cis) alkyl ester as a tert-butyl ester (R=tert-butyl) which can be selectively converted (under acid conditions) to give the free acid which can, after conversion to the acid halide, be esterified to a pesticidal (1R,cis) ester.

The (1R,cis) alkyl esters of the present invention can also be prepared by treating an ester of (1R,cis)-caronaldehyde of formula IV

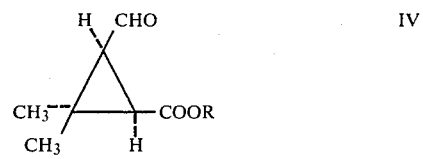

where R is an alkyl group, with hydroxylamine or an O-substituted hydroxylamine of formula $R^1ONH_2$ where $R^1$ is as defined above, and in the case where $R^1$ represents hydrogen, subsequently hydrocarbylating the resulting oxime, if desired, with an alkyl halide or the like, to give an alkoxime. Oxime formation can take place by treating substantially equimolar amounts of aldehyde and hydroxylamine or hydrocarbyloxyamine in a polar solvent such as an alkanol, e.g. ethanol or dioxane. When the aldehyde is converted into the oxime by reaction with hydroxylamine and it is desired to convert the resulting oxime into an alkylated derivative or the like, this reaction may be carried out by procedures customarily used for the alkylation of phenols. Thus, the oxime may be treated in a polar solvent, such as ethanol, with an alkyl halide, typically the bromide, in the presence of a hydrogen halide acceptor and the mixture heated until reaction is complete.

Oxime formation is normally carried out using an acid addition salt of hydroxylamine or the hydrocarbyloxyamine, e.g. the hydrochloride. It is convenient to form the oxime first and subsequently to hydrocarbylate the oxime. Certain analogs cannot be prepared by alkylation of the =NOH, e.g. neopentyl and t-butyl.

Alcohols of formula RQ where R is a group of formula II may be prepared by reduction of the corresponding acids or esters or aldehyde, e.g. with hydride, or by conversion of the corresponding halide to an ester, e.g. by reaction with sodium acetate, followed by hydrolysis of the ester or by reaction of formaldehyde with a Grignard reagent derived from an appropriate halide. The halides of formula RQ where R is a group of formula II minus D can be prepared by halomethylation of the compound

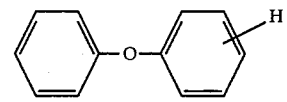

or side chain halogenation of

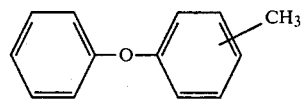

Alternatively, in another modification, the compounds of the invention are prepared by treating (1R,cis)-caronaldehydic acid previously described in U.S. Pat. No. 3,723,469 and having the formula

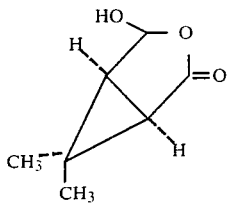

with an O-substituted hydroxylamine salt of the formula R¹ONH₃—wherein R¹ is as defined above and W is the anion of salt-forming inorganic acid. Suitable inorganic acids include hydrohalogenic acids such as hydrochloric and hydrobromic, sulfur acids such as sulfuric, and phosphorus acids such as phosphoric. Organic acids, such as oxalic acid and the like, are also suitable to form salts.

The reaction is preferably conducted in an aqueous medium in the presence of a buffer, such as an alkali metal salt of a polybasic acid, including sodium hydrogen carbonate, potassium hydrogen tartrate, disodium hydrogen phosphate and the like. Generally, at least one mole of buffer is used for each mole of (1R,cis)-caronaldehydic acid.

The molar ratio of reactants is not critical and can be widely varied, generally a molar ratio of the O-substituted hydroxylamine salt to (1R,cis)-caronaldehydic acid is suitably from about 1.0 to about 1.5 and preferably from about 1.02 to about 1.3.

The reaction is generally conducted in the liquid phase by agitating, e.g., stirring, a mixture of the reactants. The resulting product is recovered by conventional techniques such as filtering, extracting or the like.

The reaction temperature is not critical and can easily range from ambient to the reflux temperature of any solvent employed at normal pressure. Generally, the temperature is between about 0° C. to about 50° C.

A minor amount of co-solvent can be used in the reaction medium. Suitable co-solvents are lower alcohols containing from 1 to 6 carbon atoms, such as methanol, ethanol and the like.

The resulting (1R,cis)-acids are converted to the ester compounds of the invention, for example, by reaction with the arylmethyl halide, in the presence of triethylamine, in a solvent, such as refluxing ethyl acetate.

An isomer mixture of the (1R,cis) esters of the invention are readily separated into the individual diastereoisomers using known procedures, as for example, by preparative scale liquid chromatography. One such chromatographic system which can be employed has the following characteristics:
Column—porisil polar bonded phase, 9.2×250 mm
Mobile Phase—8% v/v diethyl ether in n-hexane
Flow Rate—2.5 ml/mm
Detection—UV₂₅₄ at 2.0 AUFS
Injection—typically 500 ml of a 20 mg/ml solution in the mobile phase.
Such a procedure readily yields the single diastereoisomers in greater than 90% purity (as determined by NMR analysis). In the case of (1R,cis) esters of α-substituted alcohols four diastereoisomers are obtained.

Since it has been discovered that the (1R,cis) esters of the invention in which the oxime substituent is in the Z-isomer form are pesticidally more active than when the oxime substituent is in either the E-isomer form or is a mixture of E- and Z-isomer forms, it can be desirable to convert the esters in E-isomer form into a mixture of esters in both the E- and Z-isomer forms. Such conversion is accomplished by the addition of a minor amount of an organic or inorganic acidic material. Any inorganic or organic acid or acidic acting material can be used, including acidic clays such as acidic silicates and aluminates or synthetic acidified clays, mineral acids such as hydrochloric or sulfuric acid, sulfonic acids such as toluenesulfonic acid, or organic acids, including lower alkanoic acids such as acetic, propionic or butyric acids. The acid can be used in a solid or liquid form. While the precise amount of acid used to convert the E-isomer or Z-isomer into the E- and Z-isomer mixture can vary depending on the particular oxyimino-substituted (1R,cis) ester, from 0.001 to 5% by weight of acid based on the E-isomer or Z-isomer is generally sufficient. Preferably, from 0.01 to 5% by weight of acid is used.

The invention includes, within its scope, pesticidal compositions comprising a pesticidally acceptable adjuvant—that is, at least one carrier or a surface-active agent—and, as active ingredient, at least one pesticidally active (1R,cis) ester of this invention. Likewise, the invention includes also a method of combatting insect, acarine or other arthropod pests at a locus which comprises applying to the pests or to the locus a pesticidally effective amount of at least one compound of the invention.

With respect to the spectrum of pesticidal activity, the compounds of this invention exhibit a selective or non-selective activity on such orders as Coleoptera, Lepidoptera (especially larvae), Diptera, Orthoptera, Hemiptera, Homoptera and Acarina depending upon a specific combination of acid and an alcohol according to the present invention. The compositions according to the present invention are very useful for controlling disease carrying insects such as mosquitoes, flies and cockroaches, grain insects such as rice weevil (*Sitophilus oryzae*) and mites as well as agricultural noxious insects such as planthoppers, green rice leafhopper (*Nephotettix bipuntatus cinticeps* Uhler), diamond-back moths (*Plutella maculipennis* Curtis), imported cabbage worm (*Pieris rapae* Linne), rice stem borers (*Chilo suppressalis* Walker), corn earworm larvae (*Heliothis zea* Boddie), aphids, tortrixes, leaf-miners and the like.

The (1R,cis) esters are used for harvested crops, horticultural application, forests, cultures in green house, and packaging materials for foodstuffs, household applications and as ectoparasiticides.

The term "carrier" as used herein means a material, that may be inorganic or organic and of synthetic or natural origin with which the active compound is mixed or formulated to facilitate its application to the plant, seed, soil and other object to be treated, or its storage, transport or handling. The carrier may be a solid or a liquid.

Suitable solid carriers may be natural and synthetic clays and silicates, for example, natural silicas such as diatomaceous earths; magnesium silicates, for example, talcs; magnesium aluminum silicates, for example, attapulgites and vermiculites; aluminum silicates, for example, kaolinites, montmorillonites and micas; calcium carbonate; calcium sulfate; synthetic hydrated silicon oxides and synthetic calcium or aluminum silicates; elements such as for example, carbon and sulfur; natural and synthetic resins such as, for example, coumarone resins, polyvinyl chloride and styrene polymers and copolymers; solid polychlorophenols; bitumen, waxes such as beeswax, paraffin wax, and chlorinated mineral waxes; degradable organic solids, such as ground corn cobs and walnut shells; and solid fertilizers, for example superphosphates.

Suitable liquid carriers include solvents for the compounds of this invention and liquids in which the toxicant is insoluble or only slightly soluble.

Examples of such solvents and liquid carriers, generally, are water, alcohols, for example, isopropyl alcohol, ketones, such as acetone, methyl ethyl ketone, methyl isobutyl ketone and cyclohexanone; ethers; aromatic hydrocarbons such as benzene, toluene and xylene; petroleum fractions, such as kerosene, light mineral oils, chlorinated hydrocarbons, such as methylene chloride, perchlorethylene, trichloroethane, including liquified normally vaporous gaseous compounds. Mixtures of different liquids are often suitable.

If used, the surface-active agent may be an emulsifying agent or a dispersing agent or a wetting agent. It may be nonionic, ionic or preferably, mixtures of both. Surface-active agents usually applied in formulating pesticides may be used. Examples of such surface-active agents are the sodium or calcium salts of polyacrylic acids and lignin sulfonic acids; the condensation products of fatty acids or aliphatic amines or amides containing at least 12 carbon atoms in the molecule with ethylene oxide and/or propylene oxide; fatty acid esters of glycerol, sorbitan, sucrose or pentaerythritol; fatty acids salts of low molecular weight, mono-, di- and trialkyl-amines; condensates of these with ethylene oxide and/or propylene oxide; condensation products of fatty alcohols or alkyl phenols, for example, p-octylphenol or p-octylcresol, with ethylene oxide and/or propylene oxide; sulfates or sulfonates of these condensation products; alkali or alkaline earth metal salts, preferably sodium salts of sulfonated castor oil, and sodium alkylaryl sulfonates such as sodium dodecylbenzene sulfonate; and polymers of ethylene oxide and copolymers of ethylene oxide and propylene oxide.

The compositions of the invention may be formulated as wettable powders, dusts, granules, solutions, emulsifiable concentrates, emulsions, suspension concentrates or aerosols. Encapsulated formulations and controlled release formulations are also contemplated, as are bait formulations. Wettable powders are usually compounded to contain 25, 50 or 75% w of toxicant and usually contain, in addition to solid carrier, 3-10% w of stabilizer(s) and/or other additives such as penetrants or stickers. Dusts are usually formulated as a dust concentrate having a similar composition to that of a wettable powder but without dispersant, and are diluted in the field with further solid carrier to give a composition usually containing ½-10% w of toxicant. Granules may be manufactured by extrusion of plastics, agglomeration or impregnation techniques. Generally, granules will contain ½-25% w toxicant and 0-10% w of additives such as stabilizers, slow release modifiers and binding agents. Emulsifiable concentrates usually contain, in addition to the solvent, and when necessary, cosolvent 10-50% w/v toxicant, 2-20% w/v emulsifiers and 0-20% w/v of appropriate additives such as stabilizers, penetrants and corrosion inhibitors. Suspension concentrates are compounded so as to obtain a stable, non-sedimenting, flowable product and usually contain 10-75% w toxicant, 0-5% w of dispersing agents, 0.1-10% w of suspending agents such as protective colloids and thixotropic agents, 0-10% w of appropriate additives such as defoamers, corrosion inhibitors, stabilizers, penetrants and stickers, and as carrier, water or an organic liquid in which the toxicant is substantially insoluble; certain organic additives or inorganic salts may be dissolved in the carrier to assist in preventing sedimentation or as antifreeze agents for water.

Aqueous dispersions and emulsions, for example, compositions obtained by diluting a wettable powder or an emulsifiable concentrate according to the invention with water, also lie within the scope of the present invention.

The compositions of the invention can also contain other ingredients, for example, other compounds possessing pesticidal, herbicidal or fungicidal properties, or attractants, such as pheromones, attractive food ingredients, and the like, for use in baits and trap formulations.

Particularly useful compositions can be obtained by using a mixture of two or more kinds of the present compounds, or by the use of synergists, such as those known for use with the general class of "pyrethroid" compounds, especially $\alpha$[2-(2-butoxyethoxy)ethoxy]-4,5-methylenedioxy-2-propyltoluene also known as piperonyl butoxide, 1,2-methylenedioxy-4-[2-(octylsulfinyl)propyl]benzene, 4-(3,4-methylenedioxyphenyl)-5-methyl-1,3-dioxane also known as safroxane, N-(2-ethyhexyl)bicyclo-[2,2,1]hept-5-ene-2,3-dicarboximide, octachlorodipropyl ether, isobornyl thiocyanoacetate, and other synergists used for allethrin and pyrethrin. Useful compositions can be prepared with other biological chemicals including other cyclopropanecarboxylates, organic phosphate-type insecticides and carbamate-type insecticides.

The compositions of the invention are applied in sufficient amount to supply the effective dosage of toxicant at the locus to be protected. This dosage is dependent upon many factors, including the carrier employed, the method and conditions of application, whether the formulation is present at the locus in the form of an aerosol, or as a film, or as discrete particles, the thickness of film or size of particles, the insect or acarine species to be controlled and the like, proper consideration and resolution of these factors to provide the necessary dosage of active material at the locus being within the skill of those versed in the art. In general, however, the effective dosage of toxicants of this ivention at the locus to be protected—i.e. the applied dosage—is of the order or 0.01% to 0.5% based on the total weight of the formulation, though under some circumstances the effective concentration will be as little as 0.001% or as much as 2%, on the same basis.

The superior activity of the (1R,cis) esters of the invention is usefully employed when such an ester is present in an amount substantially greater than that usually present in the racemate of an oxyimino substituted ester. Therefore, use of the (1R,cis) esters of the invention in a form substantially free of other stereoisomers is preferred, for example in a (1R, cis) isomer purity of greater than about 85%, preferably in a (1R,cis) isomer purity greater than about 90% or even greater than 95%.

ILLUSTRATIVE EMBODIMENTS

The invention is illustrated by the following embodiments which describe the preparation and biological testing of typical species of the invention with respect to representative insects and acarines. The embodiments are presented for the purpose of illustration only and should not be regarded as limiting the invention in any way. The identity of the products, including intermediates, was confirmed by elemental, infrared and nuclear magnetic resonance spectral (NMR) analyses as necessary.

EMBODIMENT 1

(1R,cis)-2,2-dimethyl-3-((isobutoxyimino)methyl)cyclopropanecarboxylic acid

A solution of 1.7 g of (1R,cis)-caronaldehydic acid and 1.6 g of isobutoxyamine hydrochloride in 50 ml of water was stirred at room temperature for 5 hours in the presence of 2.2 g of sodium bicarbonate. The resulting mixture was filtered through celite, the filtrate was acidified with concentrated hydrochloric acid, the resulting solution was extracted with methylene chloride, and the combined extracts were dried over magnesium sulfate and stripped to give 2.4 g of desired produce as an oil; $[\alpha]_D^{25} + 33.2°$ (CHCl$_3$; c=0.02 g/cc).

EMBODIMENT 2

α-Cyano-3-phenoxybenzyl (1R,cis)-2,2-dimethyl-3-((isobutoxyimino)methyl)cyclopropanecarboxylate A solution of 2.1 g of (1R,cis)-2,2-dimethyl-3-(isobutoxyimino)methyl)cyclopropanecarboxylic acid, 2.9 g of α-cyano-3-phenoxybenzyl bromide, 1 g of triethylamine and 25 ml of ethyl acetate was refluxed for about three hours and allowed to stand at room temperature for two days. The reaction mixture was diluted with methylene chloride and washed with water. The methylene chloride phase was then dried over magnesium sulfate and stripped to give 5 g of amber oil. This oil was chromatographed on a 3 foot silica gel column with a mixture of ether-pentane (1:15 ratio) as the eluant to give a yellow oil. Rechromatographing this product with a 1:9 ratio of ether-pentane as the eluant gave 3.4 g of product as a yellow oil; $[\alpha]_D^{25} + 12.1°$ (CHCl$_3$; c=0.02 g/cc).

EMBODIMENT 3

α-Cyano-3-phenoxybenzyl (1R,cis)-2,2-dimethyl-3-((neopentoxyimino)methyl)cyclopropanecarboxylate A solution of 1.4 g of (1R,cis)-2,2-dimethyl-3-((neopentoxyimino)methyl)cyclopropanecarboxylic acid in 10 ml of toluene was added to a mixture of 0.05 g of tetrabutylammonium hydrogen sulfate, 0.05 g benzyltriethylammonium chloride, 0.42 g potassium carbonate in 6 ml water. 1.6 g of α-cyano-3-phenoxybenzyl bromide was added and the resulting mixture was vigorously stirred for 6 hours at 70°-75° C., then allowed to separate into layers. The toluene layer was washed with water, then with saturated sodium bicarbonate solution and finally with saturated sodium chloride solution. The resulting solution was dried over magnesium sulfate and stripped to give an oil. This oil was chromatographed on silica gel with a mixture of ether-pentane (4:1 ratio) as the eluent to give 2.2 g of a thick yellow oil $[\alpha]_D^{25} + 7.5°$ (CHCl$_3$; c=0.02 g/cc). The (1R,cis)-2,2-dimethyl-3-((neopentoxyimino)methyl)cyclopropanecarboxylic acid was prepared by a method similar to that used in Example 1 such that neopentoxyamine hydrochloride was reacted with (1R,cis)-caronaldehydic acid.

EMBODIMENTS 4-26

Procedures similar to those of Embodiments 1-3 were used to prepare additional compounds of the invention shown in Table 1 below:

TABLE 1

OXYIMINO-SUBSTITUTED (1R,CIS)-CYCLOPROPANECARBOXYLATES

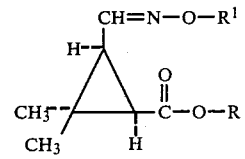

| Embodiment | R$^1$ | R | Isomer Z/E | $[\alpha]_D^{25}$(CHCl$_3$) c = 0.02 g/cc |
|---|---|---|---|---|
| 4 | —CH(CH$_3$)$_2$ | α-cyano-3-phenoxybenzyl | E-Z-isomer | +19.6° |
| 5 | —CH(CH$_3$)C$_2$H$_5$ | α-cyano-3-phenoxybenzyl | E-Z-isomer | +23.8° |
| 6 | -n-C$_3$H$_7$ | α-cyano-3-phenoxybenzyl | E-Z-isomer | +16.7° |
| 7 | -n-C$_4$H$_9$ | α-cyano-3-phenoxybenzyl | E-Z-isomer | +20.0° |
| 8 | —C(CH$_3$)$_3$ | α-cyano-3-phenoxybenzyl | E-Z-isomer | +17.5° |
| 9 | —CH$_2$(CH$_2$)$_4$CH$_3$ | α-cyano-3-phenoxybenzyl | E-Z-isomer | not det. |
| 10 | —CH$_2$(CH$_2$)$_4$CH$_3$ | α-cyano-3-phenoxybenzyl | E-Z-isomer | +5.0° |
| 11a | —CH$_2$CH(CH$_3$)$_2$ | 3-phenoxybenzyl | E-Z-isomer | +5.0° |
| 11b | —CH$_2$CH(CH$_3$)$_2$ | 3-phenoxybenzyl | E-isomer | +21.2° |
| 11c | —CH$_2$CH(CH$_3$)$_2$ | 3-phenoxybenzyl | Z-isomer | +23.8° |
| 12 | —CH$_2$CH$_2$CH(CH$_3$)$_2$ | α-cyano-3-phenoxybenzyl | E-Z-isomer | +10.0° |
| 13 | —CH$_2$CH(CH$_3$)CH$_2$CH$_3$ | α-cyano-3-phenoxybenzyl | E-Z-isomer | +6.2° |
| 15 | —CHCH(CH$_3$)CH$_2$CH$_3$ (single isomer configuration in R$^1$) | α-cyano-3-phenoxybenzyl | | +12.5 |
| 16 | —CH$_2$C(CH$_3$)$_3$ | 3-phenoxybenzyl | | +7.5° |
| 17 | —CH(CH$_3$)$_2$ | H | | +45.4° |
| 18 | —C(CH$_3$)$_3$ | H | | +40.0° |
| 19 | —(CH$_2$)$_3$CH$_3$ | H | | +30.6° |
| 20 | —(CH$_2$)$_4$CH$_3$ | H | | +22.5° |
| 21 | —(CH$_2$)$_5$CH$_3$ | H | | +22.5° |
| 22 | —CH$_2$—CH$_2$—CH(CH$_3$)$_2$ | H | | +22.5° |
| 23 | —CH$_2$CH(CH$_3$)CH$_2$CH$_3$ | H | | +18.8° |
| 24 | —CH$_2$CH(CH$_3$)$_2$ | (CH$_2$)$_{15}$CH$_3$ | | |
| 25 | —CH$_2$CH(CH$_3$)CH$_2$CH$_3$ | H | | +31.2° |

TABLE 1-continued
OXYIMINO-SUBSTITUTED (1R,CIS)-CYCLOPROPANECARBOXYLATES

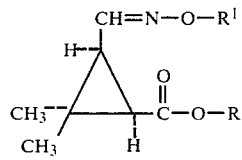

| Embodiment | R¹ | R | Isomer Z/E | $[\alpha]_D^{25}$(CHCl₃) c = 0.02 g/cc |
|---|---|---|---|---|
| 26 | —CH₂C(CH₃)₃ | H | | +12.5° |

EMBODIMENT 27

Diastereoisomers of α-cyano-3-phenoxybenzyl (1R,cis)-2,2-dimethyl-3-((isopropoxyimino)methyl)cyclopropanecarboxylate An isomer mixture of R,S-α-cyano-3-phenoxybenzyl (1R,cis)-2,2-dimethyl-3-((isopropoxyimino)methyl)cyclopropanecarboxylate (E-Z mixture), prepared as in Embodiment 6 above, was separated into its four (4) diastereoisomeric forms using a preparative scale liquid chromatograph (LC). The chromatographic system employed was:

Column—porisil polar bonded phase 9.2×250 mm.
Mobile Phase—8% v/v diethyl ether in n-hexane.
Flow Rate—2.5 ml/min.
Detection—UV₂₅₄ at AUFS.
Injection—typically 500 ml of a 20 mg/ml solution in the mobile phase.

The individual diastereoisomers were isolated in greater than 90% purity (as determined by NMR analysis) and are set forth in Table 2 below in terms of their stereoisomeric configuration and column retention time.

TABLE 2
DIASTEREOISOMERS OF α-CYANO-3-PHENOXYBENZYL (1R,CIS)-2,2-DIMETHYL-3-((ISOPROPOXYIMINO)-METHYL)CYCLOPROPANECARBOXYLATE

| Embodiment | Configuration Oxime | Configuration Alcohol | Retention Time (min) |
|---|---|---|---|
| 27a | E | R | 6.6 |
| 27b | E | S | 7.8 |
| 27c | Z | R | 7.2 |
| 27d | Z | S | 8.4 |

Following procedures similar to Embodiment 27 above: α-cyano-3-phenoxybenzyl (1R,cis)-2,2-dimethyl-3-((n-butoxyimino)methyl)cyclopropanecarboxylate, α-cyano-3-phenoxybenzyl (1R,cis)-2,2-dimethyl-3-((n-pentoxyimino)methyl)cyclopropanecarboxylate, α-cyano-3-phenoxybenzyl (1R,cis)-2,2-dimethyl-3-((2-methylpentoxyimino)methyl)cyclopropanecarboxylate, α-cyano-3-phenoxybenzyl (1-R,cis)-2,2-dimethyl-3-((n-propoxyimino)methyl)cyclopropanecarboxylate, and α-cyano-3-phenoxybenzyl (1r,cis)-2,2-dimethyl-3-((isoamyloxyimino)methyl)cyclopropanecarboxylate are separated into their individual diastereoisomers.

EMBODIMENT 28

Pesticidal Activity

Activity of the compounds of this invention with respect to insect and acarine pests was determined by using standardized test methods to test the toxicity of the compounds as follows:

I. Houseflies (*Musca domestica*(Linne)) were tested by placing 50 4- to 5-day old houseflies into a spray cage and spraying with 0.6 ml of a solution of test compound. After spraying, the flies were anesthetized with CO₂ and transferred to a recovery cage containing a milk pad for food. The cages were held for 18–20 hours after which mortality counts were made. Both dead and moribund were counted. The tests were conducted employing several different dosage rates of each test compound.

II. Pea aphids (*Acyrthosiphon pisum* (Harris)) were tested by placing about 100 aphids on broad bean plants. The plants were sprayed with dilutions of acetone solution of test compound into water containing an emulsifier and held in containers under laboratory conditions for 18 to 20 hours at which time the living aphids in the containers were counted. The tests were conducted employing several different dosage rates of each test compound.

III. Adult female two-spotted spider mites (*Tetranychus urticae* (Koch)) were tested by placing 50–75 mites on the bottom side of leaves of pinto bean plants. The leaves were sprayed with dilutions of acetone solution of test compound into water containing an emulsifier and kept under laboratory conditions for about 20 hours at which time mortality counts were made. The test were conducted employing several different dosage rates of test compounds.

IV. Mosquito larvae (*Anopheles albimanus* (Weide)) were tested by placing ten living and active mosquito larvae in a jar containing a 0.1 ml aliquot of a 1% acetone solution of test compound thoroughly mixed with 100 ml of distilled water. After 18–22 hours, mortality counts were taken. Both dead and moribund larvae were counted as dead. Larvae which did not swim after being prodded with a needle were considered moribund. The tests were conducted employing several different dosage rate for each test compound.

V. Corn earworm larvae (*Heliothis zea* (Boddie)) were tested by spraying a broad bean plant with dilutions of acetone solution of test compound into water containing an emulsifier. Immediately after spraying, 5 larvae were transferred to the plant and held for 44–46 hours, at which time the dead and moribund larvae were counted. The tests were coducted employing several different dosage rates for each test compound.

In each instance, the toxicity of the compound of the invention was compared to that of a standard pesticide (Parathion), its relative toxicity then being expressed in terms of the relationship between the amount of compound of the invention and the amount of the standard pesticide required to produce the same percentage (50) of mortality in the test insects or acarine. By assigning the standard pesticide an arbitrary rating of 100, the toxicities of the compounds of the invention were expressed in terms of the toxicity indexes, which compares the toxicity of the compounds of the invention with that of the standard pesticide. That is to say, a test compound having a Toxicity Index of 50 would be half as active, while one having a Toxicity Index of 200 would be twice as active as the standard pesticide.

Results of the above tests are shown in Table 3.

It can be seen that the compounds of the invention exhibit toxicity against the various pests tested and were particularly effective on corn earworm larvae. Moreover, a number of compounds of the invention are particularly effective for controlling acarines, such as the two-spotted spider mites as indicated by the compound having a Toxicity Index against mites of about 100 or greater, for example, the compounds of Embodiment 27c (the Z-isomer of 3-phenoxybenzyl (1R,cis)-2,2-dimethyl-3-((isobutoxyimino)methyl)cyclopropanecarboxylate).

TABLE 3

PESTICIDAL ACTIVITY OF (1R,CIS)CYCLOPROPANE-
CARBOXYLATE OXIMES EXPRESSED AS TOXICITY
INDEX RELATIVE TO THAT OF
PARATHION AS A STANDARD EQUAL TO 100

| Embodiment | House Fly | Pea Aphid | 2-Spotted Mite | Mosquito Larvae | Corn Earworm |
|---|---|---|---|---|---|
| 4 | 210 | 370 | 26 | — | 550 |
| 5 | — | 140 | 55 | — | 670 |
| 3 | 550 | 6,300 | 860 | 400 | 3,200 |
| 27b | — | — | — | — | 1,700 |
| 27d | — | — | — | — | 2,400 |
| 6 | 270 | 250 | 20 | 1,400 | 300 |
| 9 | 650 | 450 | 55 | 4,300 | 390 |
| 2 | 760 | 1,300 | 80 | 3,500 | 1,100 |
| 7 | 520 | 690 | 34 | 4,200 | 920 |
| 8 | 110 | 440 | 82 | 500 | 470 |
| 12 | 300 | 440 | 69 | 450 | 330 |
| 13 | 440 | 690 | 140 | 3,000 | 550 |
| 11a | — | — | — | — | 560 |
| 11b | 41 | 48 | 40 | 24 | 230 |
| 11c | 290 | 230 | 310 | 360 | 1,300 |
| 15 | 250 | 880 | 120 | 57 | 900 |
| 16 | 44 | 81 | 590 | 33 | 1,600 |

— indicates no test.

Moreoever, the (1R,cis) compounds of the invention have been found to be unexpectedly more active in the control of certain pests, particularly the corn earworm larvae and mites, than the corresponding structurally most similar (1R,trans) compounds specifically disclosed in U.S. Pat. No. 3,922,269.

We claim:

1. A (1R,cis)-cyclopropane compound, substantially free of other stereoisomers, having the formula

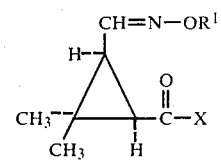

wherein $R^1$ is an alkyl group containing from 3 to 6 carbon atoms and X is OR in which R is α-cyano-3-phenoxybenzyl or 3-phenoxybenzyl, with the proviso that when R is α-cyano-3-phenoxybenzyl then the alcohol moiety is in the R,S-racemic or S-optical configuration.

2. A (1R,cis) compound according to claim 1 wherein $R^1$ is an alkyl group containing 4 or 5 carbon atoms.

3. A (1R,cis) compound according to claim 2 wherein $R^1$ is isobutyl.

4. A (1R,cis) compound according to claim 2 wherein $R^1$ is neopentyl.

5. A (1R,cis) compound according to claim 2 wherein R is 2-methylbutyl.

6. A (1R,cis) compound according to claims 3, 4 or 5 wherein R is α-cyano-3-phenoxybenzyl.

7. A (1R,cis) compound according to claims 3, 4 or 5 wherein R is 3-phenoxybenzyl.

8. A (1R,cis) compound according to claims 1 or 2 wherein the oxime substituent is substantially in the Z-isomer form.

9. A pesticidal composition comprising a pesticidally effective amount of an oxyimino-substituted (1R,cis)cyclopropane compound according to claim 1 and at least one agriculturally acceptable surface-active agent or carrier therefor.

10. A method of controlling pests at a locus which comprises applying to the pests or to the locus a pesticidally effective amount of an oxyimino-substituted (1R,cis)cyclopropane carboxylate according to claim 1.

11. A method according to claim 10 wherein the pests are selected from the order Coleoptera, Lepidoptera, Diptera, Orthoptera, Hemiptera, Homoptera or Acarina.

12. A method according to claim 11 wherein the pests are larvae of the order Lepidoptera.

13. A method according to claim 11 wherein the pests are of the order Acarina.

14. A (1R,cis)-cyclopropane compound, substantially free of other stereoisomers, having the formula

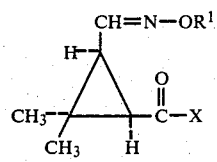

wherein $R^1$ is an alkyl group containing from 3 to 6 carbon atoms and X is chlorine, bromine or OR in which R is a hydrogen atom, a salt-forming cation or an alkyl group containing from 1–20 carbon atoms.

* * * * *